United States Patent
Desai et al.

(10) Patent No.: US 9,814,890 B2
(45) Date of Patent: Nov. 14, 2017

(54) STYRENE-ISOBUTYLENE COPOLYMERS AND MEDICAL DEVICES CONTAINING THE SAME

(71) Applicant: Cardiac Pacemakers, Inc., St. Paul, MN (US)

(72) Inventors: Shrojalkumar Desai, Lake Bluff, IL (US); Daniel J. Cooke, Roseville, MN (US); G. Shantanu Reddy, Minneapolis, MN (US); Mohan Krishnan, Shoreview, MN (US); Michael C. Smith, Lino Lakes, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 14/939,505

(22) Filed: Nov. 12, 2015

(65) Prior Publication Data
US 2016/0059018 A1   Mar. 3, 2016

Related U.S. Application Data

(62) Division of application No. 12/563,733, filed on Sep. 21, 2009, now Pat. No. 9,205,271.

(60) Provisional application No. 61/099,064, filed on Sep. 22, 2008.

(51) Int. Cl.
| *A61N 1/375* | (2006.01) |
| *A61N 1/05* | (2006.01) |
| *C08L 53/00* | (2006.01) |
| *C08L 75/08* | (2006.01) |

(52) U.S. Cl.
CPC .............. *A61N 1/375* (2013.01); *A61N 1/05* (2013.01); *C08L 53/00* (2013.01); *C08L 75/08* (2013.01)

(58) Field of Classification Search
CPC A61N 1/05; A61N 1/375; C08L 53/00; C08L 53/005; C08L 75/08
See application file for complete search history.

(56) References Cited

U.S. PATENT DOCUMENTS

| 5,358,516 A | 10/1994 | Myers et al. |
| 5,630,844 A | 5/1997 | Dogan et al. |
| 5,741,331 A | 4/1998 | Pinchuk |
| 5,861,023 A | 1/1999 | Vachon |
| 5,921,933 A | 7/1999 | Sarkis et al. |
| 6,197,240 B1 | 3/2001 | Pinchuk |
| 6,545,097 B2 | 4/2003 | Pinchuk et al. |

(Continued)

FOREIGN PATENT DOCUMENTS

| AU | 2009292958 B2 | 3/2010 |
| EP | 2344238 A2 | 7/2011 |

(Continued)

OTHER PUBLICATIONS

International Preliminary Report on Patentability issued in PCT/2009/057679, dated Mar. 22, 2011, 10 pages.

(Continued)

*Primary Examiner* — Tammie K Heller
(74) *Attorney, Agent, or Firm* — Faegre Baker Daniels LLP (57) ABSTRACT

In accordance with various aspects of the invention, copolymers comprising styrene and isobutylene monomers are used in the construction of implantable and insertable medical devices for electrical stimulation, including, for example, electronic signal generating components and electrical leads for such devices.

20 Claims, 2 Drawing Sheets

(56) References Cited

U.S. PATENT DOCUMENTS

| | | | |
|---|---|---|---|
| 7,289,846 | B2 | 10/2007 | Shoberg et al. |
| 7,347,751 | B2 | 3/2008 | Sweeney et al. |
| 7,715,922 | B1 | 5/2010 | Tan |
| 8,751,018 | B1 | 6/2014 | Dorab et al. |
| 9,205,271 | B2 | 12/2015 | Desai et al. |
| 2002/0107330 | A1 | 8/2002 | Pinchuk et al. |
| 2002/0198601 | A1 | 12/2002 | Bales et al. |
| 2003/0108659 | A1 | 6/2003 | Bales et al. |
| 2003/0171496 | A1 | 9/2003 | Pinchuk et al. |
| 2005/0027342 | A1 | 2/2005 | Shoberg et al. |
| 2005/0225803 | A1 | 10/2005 | Enomoto |
| 2006/0111626 | A1 | 5/2006 | Rossing et al. |
| 2007/0224239 | A1 | 9/2007 | Behan et al. |
| 2008/0033423 | A1 | 2/2008 | Peacock |
| 2008/0286333 | A1 | 11/2008 | Kangas et al. |
| 2009/0062896 | A1 | 3/2009 | Overstreet et al. |
| 2009/0123521 | A1 | 5/2009 | Weber et al. |
| 2010/0256720 | A1 | 10/2010 | Overstreet et al. |

FOREIGN PATENT DOCUMENTS

| | | | |
|---|---|---|---|
| JP | 08504341 | A | 5/1996 |
| JP | 2002522167 | A | 7/2002 |
| JP | 2012502769 | A | 2/2012 |
| WO | WO9413358 | A1 | 6/1994 |
| WO | WO0009178 | A1 | 2/2000 |
| WO | 2010033911 | A2 | 3/2010 |

OTHER PUBLICATIONS

Pinchuk et al., Medical applications of poly(styrene-block-isobutylene-block-styrene) ("SIBS"), Biomaterials 29 (2008) pp. 448-460.

Ranade, S. et al., "Physical characterization of controlled release of paclitaxel from the TAXUS™ Express2™ drug-eluting stent", Journal of Biomedical Materials Research Part A, 71A (2004) 625-634.

Gorce, Jean-Noel et al. "Mechanical Hysteresis of a Polyether." Polymer Engineering and Science, Sep. 1993, vol. 33, No. 18. 7 pages.

International Search Report and Written Opinion issued in PCT/US2009/057679, dated Jun. 9, 2010, 15 pages.

Kwee, Tety et al. "Morphology and mechanical and dynamic mechanical properties of linear and star poly(styrene-b-isobutylene-b-styrene) block copolymers." ScienceDirect, School of Polymers and High Performance Materials, The University of Southern Mississippi, vol. 46, Issue 12, May 26, 2005, pp. 4480-4491. 12 pages.

Pongkitwitoon, Suphannee et al. "Temperature dependent microphase mixing of model polyurethanes with different intersegment compatibilities." ScienceDirect, Polymer, vol. 50, Issue 26, Dec. 10, 2009, pp. 6305-6311. 7 pages.

Ranade, S.V. et al., Styrenic Block copolymers for Biomaterial and Drug Delivery Applications, Acta Biomater. Jan. 2005; 1(1): 137-44.

Virmani, R. et al. Circulation Feb. 17, 2004 109)6) 701-5.

STYRENE-ISOBUTYLENE COPOLYMERS AND MEDICAL DEVICES CONTAINING THE SAME

CROSS-REFERENCE TO RELATED APPLICATION

This application is a division of U.S. application Ser. No. 12/563,733, filed Sep. 21, 2009 which claims priority to Provisional Application No. 61/099,064, filed Sep. 22, 2008, which are herein incorporated by reference in their entirety.

FIELD OF THE INVENTION

The present invention relates to styrene-isobutylene copolymers and to medical devices containing the same.

BACKGROUND OF THE INVENTION

The use of polymeric materials in medical devices for implantation or insertion into the body of a patient is common in the practice of modern medicine. For example, polymeric materials such as silicone rubber, polyurethane, and fluoropolymers, for instance, polytetrafluoroethylene (PTFE), expanded PTFE (ePTFE) and ethylene tetrafluoroethylene (ETFE), are used as coating materials/insulation for medical leads, providing mechanical protection, electrical insulation, or both.

As another example, drug eluting stents are known which have polymeric coatings over the stent that release a drug to counteract the effects of in-stent restenosis. Specific examples of drug eluting coronary stents include commercially available stents from Boston Scientific Corp. (TAXUS, PROMUS), Johnson & Johnson (CYPHER), and others. See S. V. Ranade et al., Acta Biomater. 2005 January; 1(1): 137-44 and R. Virmani et al., Circulation 2004 Feb. 17, 109(6): 701-5. Various types of polymeric materials have been used in such polymeric coatings including, for example, homopolymers such as poly(n-butyl methacrylate) and copolymers such as poly(ethylene-co-vinyl acetate), poly(vinylidene fluoride-co-hexafluoropropylene), and poly(styrene-b-isobutylene-b-styrene) triblock copolymers (SIBS). SIBS triblock copolymers have a soft, elastomeric low glass transition temperature (Tg) midblock and hard elevated Tg endblocks. Consequently, SIBS copolymers are thermoplastic elastomers, in other words, elastomeric (i.e., reversibly deformable) polymers that form physical cross-links which can be reversed by melting the polymer (or, in the case of SIBS, by dissolving the polymer in a suitable solvent). SIBS is also highly biocompatible and biostable.

SUMMARY OF THE INVENTION

In accordance with various aspects of the invention, copolymers comprising styrene and isobutylene monomers are used in the construction of implantable and insertable medical devices for electrical stimulation, including, for example, electronic signal generating components and electrical leads for such devices.

Potential advantages of the present invention include one or more of the following, among others: (a) enhanced device reliability due to reduced insulator degradation and/or increased durability; (b) improved speed of manufacturing; (c) improved production yield; and (d) reduced lead size.

These and other aspects, embodiments and advantages of the present invention will become readily apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

As is well known, "polymers" are molecules containing multiple copies (e.g., from 2 to 5 to 10 to 25 to 50 to 100 to 1000 to 10,000 or more copies) of one or more constitutional units, commonly referred to as monomers. As used herein, the term "monomer" may refer to free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit (i.e., monomer). "Copolymers" are polymers that contain multiple copies of at least two dissimilar constitutional units.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" or "block" is a grouping of constitutional units (e.g., 2 to 5 to 10 to 25 to 50 to 100 to 1000 to 10,000 or more units). Blocks can be unbranched or branched. As used herein, a "chain" is a linear (unbranched) block.

In accordance with various aspects of the invention, copolymers comprising styrene and isobutylene monomers (referred to herein as "styrene/isobutylene copolymers" or "SIBC's"), including poly(styrene-co-isobutylene) copolymers and block copolymers comprising one or more polystyrene blocks and one or more polyisobutylene blocks, for example, poly(styrene-b-isobutylene) diblock copolymers, poly(styrene-b-isobutylene-b-styrene) triblock copolymers (SIBS), poly(isobutylene-b-styrene-b-isobutylene) triblock copolymers (IBSIB), as well as thermoplastic polyurethanes containing polystyrene and polyisobutylene blocks, among many other possibilities, are used in the construction of implantable and insertable medical devices.

More particularly, SIBC containing materials may be used in the construction of implantable and insertable medical devices for electrical stimulation, in accordance with various embodiments of the invention. Such devices typically include (a) an electronic signal generating component and (b) one or more leads. The electronic signal generating component commonly contains a source of electrical power (e.g., a sealed battery) and an electronic circuitry package, which produces electrical signals that are sent into the body (e.g., the heart, nervous system, etc.). Many electronic signal generating components also have the capability to receive and respond to signals that are emitted by the body (i.e., they are electronic signal generating/sensing components). Leads comprise at least one flexible elongated conductive member (e.g., a wire, cable, etc.), which is insulated along at least a portion of its length. The conductive member is adapted to place the electronic signal generating component of the device in electrical communication with one or more electrodes, which provide for electrical connection with the body. Leads are thus able to conduct electrical signals to the body from the electronic signal generating component. Leads may also relay signals from the body to the electronic signal generating component.

Figure 6:
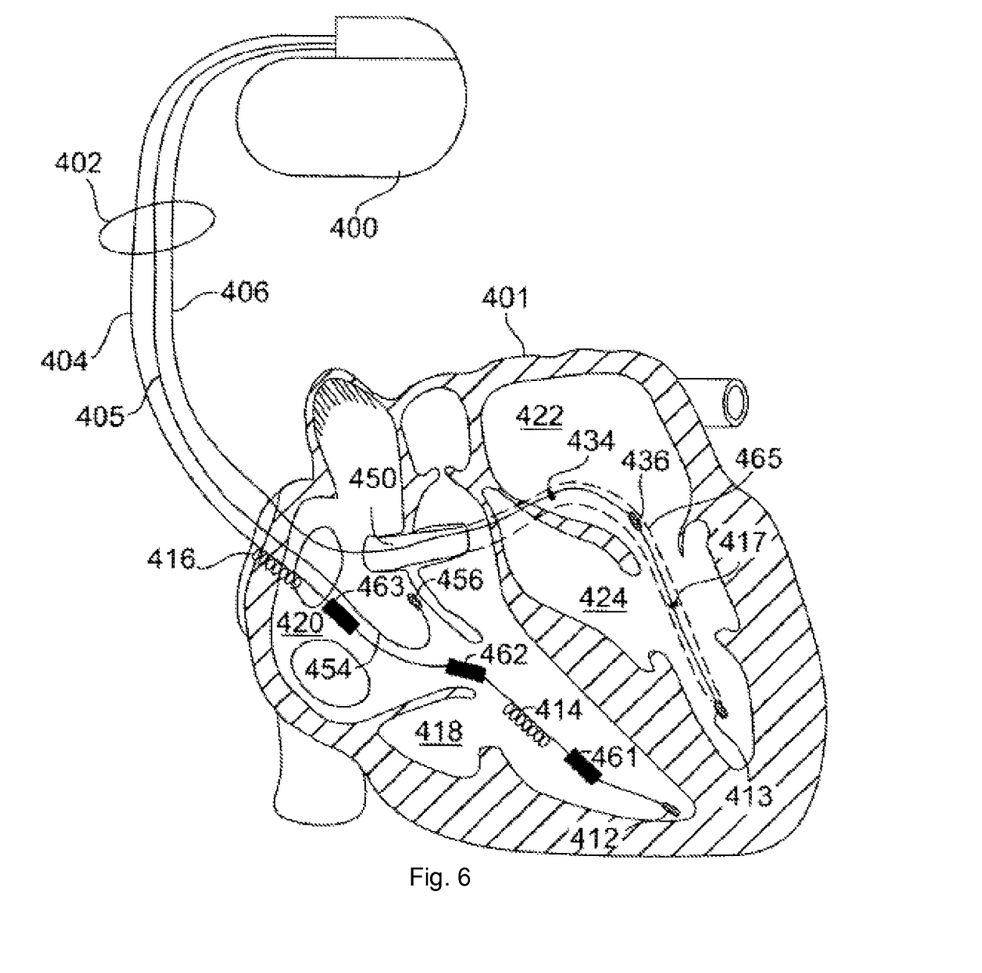
FIG. 6 is a schematic illustration of an implantable cardiac device including a lead assembly shown implanted in a sectional view of a heart, the lead assembly employing styrene-isobutylene copolymers in accordance with an embodiment of the present invention.

As a specific example, referring to FIG. 6, there is shown a patient internal medical device (PIMD) that represents one of several types of devices with electronic signal generating components and implantable leads that may benefit from the use of SIBC containing materials in accordance with various embodiments of the present invention. For example, the PIMD illustrated in FIG. 6 as a pacemaker/defibrillator, may be representative of all or part of a pacemaker, defibrillator, cardioverter, cardiac monitor, or resynchronization device (e.g., multichamber or multisite device). Accordingly, the present invention may be useful for signal generating components and leads used in a wide variety of implantable medical devices that sense and stimulate cardiac activity.

The implantable device illustrated in FIG. 6 is an embodiment of the PIMD including an electronic signal generating/sensing component 400 (specifically, an implantable pacemaker/defibrillator) electrically and physically coupled to an intracardiac lead system 402. The intracardiac lead system 402 is implanted in a human body with portions of the intracardiac lead system 402 inserted into a heart 401. Electrodes of the intracardiac lead system 402 may be used to detect and analyze cardiac signals produced by the heart 401 and to provide stimulation and/or therapy energy to the heart 401 under predetermined conditions, to treat cardiac arrhythmias of the heart 401.

The PIMD depicted in FIG. 6 is a multi-chamber device, capable of sensing signals from one or more of the right and left atria 420, 422 and the right and left ventricles 418, 424 of the heart 401 and providing pacing pulses to one or more of the right and left atria 420, 422 and the right and left ventricles 418, 424. Low energy pacing pulses may be delivered to the heart 401 to regulate the heartbeat or maintain a cardiac rhythm, for example. In a configuration that includes cardioversion/defibrillation capabilities, high-energy pulses may also be delivered to the heart 401 if an arrhythmia is detected that requires cardioversion or defibrillation.

The intracardiac lead system 402 includes a right ventricular lead system 404, a right atrial lead system 405, and a left atrial/ventricular lead system 406. The right ventricular lead system 404 includes an RV-tip pace/sense electrode 412, an RV-coil electrode 414, and one or more impedance sense/drive electrodes 461, 462, 463. In one arrangement, impedance sense and drive electrodes 461, 462, 463 are configured as ring electrodes. The impedance drive electrode 461 may be located, for example, in the right ventricle 418. The impedance sense electrode 462 may be located in the right atrium 420. Alternatively or additionally, an impedance sense electrode 463 may be located in the superior right atrium 420 or near the right atrium 420 within the superior vena cava. The RV-tip electrode 412 is positioned at an appropriate location within the right ventricle 418 for pacing the right ventricle 418 and sensing cardiac activity in the right ventricle 418. The right ventricular lead system may also include one or more defibrillation electrodes, i.e., coils 414, 416, positioned, for example, in the right ventricle 418 and the superior vena cava, respectively.

The atrial lead system 405 includes A-tip and A-ring cardiac pace/sense electrodes 456, 454. In the configuration of FIG. 6, the intracardiac lead system 402 is positioned within the heart 401, with a portion of the atrial lead system 405 extending into the right atrium 420. The A-tip and A-ring electrodes 456, 454 are positioned at an appropriate location within the right atrium 420 for pacing the right atrium 420 and sensing cardiac activity in the right atrium 420.

The lead system 402 illustrated in FIG. 6 also includes a left atrial/left ventricular lead system 406. The left atrial/left ventricular lead system 406 may include, one or more electrodes 434, 436, 417, 413 positioned within a coronary vein 465 of the heart 401. The left atrial/left ventricular lead system 406 may include, for example, one or more endocardial pace/sense leads that are advanced through the superior vena cava (SVC), the right atrium 420, the valve of the coronary sinus, and the coronary sinus 450 to locate the LA-tip 436, LA-ring 434, LV-tip 413 and LV-ring 417 electrodes at appropriate locations adjacent to the left atrium 422 and left ventricle 424, respectively. In one configuration, the left atrial/left ventricular lead system 406 is implemented as a single-pass lead. It is understood that the preceding descriptions with regard to LV-tip 413 and LV-ring 417 electrodes are equally applicable to a lead configuration employing distal and proximal LV ring electrodes (with no LV-tip electrode).

Additional configurations of sensing, pacing and defibrillation electrodes may be included in the intracardiac lead system 402 to allow for various sensing, pacing, and defibrillation capabilities of multiple heart chambers. In other configurations, the intracardiac lead system 402 may have only a single lead with electrodes positioned, for example, in the right atrium or the right ventricle to implement single chamber cardiac pacing. In yet other embodiments, the intracardiac lead system 402 may not include the left atrial/left ventricular lead 406 and may support pacing and sensing of the right atrium and right ventricle only. For further information regarding lead configurations, see, e.g., U.S. Pat. No. 7,347,751 to Sweeny et al.

Various lead and electrode arrangements and configurations in addition to the foregoing are clearly within the scope of the devices of the present invention.

As can be seen from the foregoing discussion, the present invention is applicable to a wide variety of medical devices with electronic signal generating components and implantable leads. For example, in accordance with the present invention, SIBC containing materials may be used to form lead insulation components through which at least one conductor extends, including single-lumen and multi-lumen extrusions and tubular (tube-shaped) insulation layers, as well as lead tip materials, headers, and various other lead components. SIBC containing materials may also be used as encapsulation/insulation materials for electronic signal generating/sensing components, examples of which include implantable pulse generators, implantable cardioverter-defibrillators (ICDs) and implantable cardiac resynchronization therapy (CRT) devices. Such electronic signal generating/sensing components may be used, for example, in conjunction with right ventricular lead systems, right atrial lead systems, and left atrial/ventricular lead systems and may be used to treat, for example, bradycardia, tachycardia (e.g., ventricular tachycardia) or cardiac dyssynchrony in a vertebrate subject (including humans, pets and livestock). The present invention is also applicable to leads and electronic signal generating/sensing components for neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others.

SIBC's may be synthesized according to known methods, particularly controlled/"living" cationic polymerization. For further information regarding synthesis of styrene-isobutylene copolymers, including poly(styrene-b-isobutylene-b-styrene) triblock copolymers (SIBS), see, e.g., U.S. Pat. No. 6,545,097 to Pinchuk et al. and the references cited therein.

The properties of SIBC's, including SIBS, may be modified by varying the ratio of styrene to isobutylene within the copolymer. Typically, the styrene monomer content of the styrene/isobutylene copolymers of the invention ranges from 15 to 50 mol % (e.g., from 15 to 17.5 to 20 to 22.5 to 25 to 30 to 35 to 40 to 45 to 50 mol %). Thus, where no additional monomer is provided within the copolymer, the isobutylene content of the copolymers typically ranges from 85 to 50 mol % (e.g., from 85 to 82.5 to 80 to 77.5 to 75 to 70 to 65 to 60 to 55 to 50 mol %).

In various embodiments, the styrene content will be 20 mol % or greater, and more typically 22.5 mol % or greater. This amount of styrene is greater than the amount that is typically found in the SIBS used in stent coatings (i.e., about 17 mol styrene), which coatings are typically formed on metallic stents via solution coating processes. The higher styrene content is desirable from the perspective of the present invention, for example, because it is more readily processed using thermoplastic techniques such as extrusion and because SIBS with higher styrene content is stiffer, and thus more torqueable, than low styrene content SIBS. Torqueability is frequently a desirable feature for various devices that are inserted into a subject by a physician, including electronic leads. As noted above, electronic leads commonly include lead insulation components through which at least one conductor extends, including single-lumen and multi-lumen extrusions and tubular insulation layers. By selecting stiffer materials for such insulation components, the overall torqueability of the device may be improved.

In certain embodiments, SIBC's, including SIBS, having a relatively high styrene content (i.e., from 15 to 17 to 19 to 21 mol %) are blended with SIBC's having a relatively low styrene content (i.e., from 22 to 25 to 30 to 35 to 40 to 45 to 50 mol %) to provide, for example, a desired degree of stiffness and/or processability. For example, SIBS having a relatively high styrene content can be thermally extruded with SIBS having a relatively low styrene content. In some embodiments, the high and low content SIBS are combined in a pre-blending step (e.g., extruded into the form of pellets, etc.) prior to extrusion into a final device component (e.g., a single-lumen or multi-lumen extrusion, etc.)

Thermoplastic elastomers (TPE's) other than SIBC's (referred to herein as "non-SIBC TPE's") are also used in certain embodiments of the invention. These TPE's include thermoplastic polyurethanes (TPU's), for example, polyether TPU's such as the Pellethane™ family of polyether-polyurethanes from Dow Plastics, a business unit of the Dow Chemical Company. Such polymers can assist in providing the torqueability that is desired for lead materials, particularly those TPU materials with higher isocyanate content, which leads to higher stiffness/modulus. By employing materials with higher stiffness/modulus, thinner material layers may be employed without sacrificing torqueability, allowing the size of various medical device components, including leads, to be reduced.

In addition to polyether TPU's, non-SIBC TPE's further include polycarbonate TPU's, polysiloxane TPU's, TPE's based on alkyl acrylates and/or alkyl methacrylates such as poly(methyl methacrylate-b-n-butyl acrylate-b-methyl methacrylate), and TPE's that comprise polyethylene terephthalate segments and fluorinated segments such as PTFE, ETFE, and hexafluoropropylethylene (HFP) segments, among many others.

Various TPE's, including TPU's such as those described above, however, can eventually exhibit environmental stress cracking upon insertion into a patient's body, due to the harsh (e.g., oxidative) conditions that are encountered there. Where such TPE's are employed as lead insulation materials, such cracking can cause a breach in the insulation that allows bodily fluids to enter the lead and form shorts, for example, between the conductor(s) and/or the electronic components that generate current through the conductor(s).

SIBC's, including SIBS, on the other hand, possess exceptional biostability and biocompatibility. Thus in certain embodiments of the invention, a SIBC containing material is provided over a non-SIBC TPE containing material such as a TPU containing material (which may provide, for example, desirable mechanical attributes) in order to protect the non-SIBC TPE material from the external environment.

Moreover, slow corrosion of the metal conductor(s) within electrical leads is often encountered in the in vivo environment. The metal ions thus generated from the slow corrosion process are known to react with various TPE insulation materials, including TPU's, causing metal ion oxidation (MIO) that can result in degradation and deterioration of the material. This can lead to rapid battery depletion and affect the ability of the device to reliably provide therapy. A chemically stable material could act as an excellent barrier in preventing the migration of these detrimental metal ions to the TPE insulation material. In some embodiments of the invention, a SIBC containing material is thus provided between the conductor and a non-SIBC TPE containing material, to protect the non-SIBC TPE containing material from MIO.

Based on the above and other rationales, in various embodiments of the invention, leads are formed from multiple materials, and in particular are formed from at least one SIBC containing material and at least one non-SIBC TPE containing material (e.g., a TPU containing material, etc.). Examples include leads that comprise the following among others: (a) a SIBC containing material disposed over a non-SIBC TPE containing material (e.g., to protect the non-SIBC TPE containing material from the surrounding environment), (b) a SIBC containing material disposed under a non-SIBC TPE containing material (e.g., to protect the non-SIBC TPE containing material from MIO due to an underlying conductor), (c) a SIBC containing material disposed over a non-SIBC TPE containing material which is disposed over a SIBC containing material (e.g., to protect the non-SIBC TPE containing material from the surrounding environment and from MIO due to an underlying conductor).

In a further embodiment, a non-SIBC TPE containing material is disposed over a SIBC containing material which is disposed over a non-SIBC TPE containing material.

In various embodiments, the polymer containing materials that are employed in the present invention, including SIBC containing materials and non-SIBC TPE containing materials, are blended or otherwise combined with one or more optional supplemental agents as described in more detail below.

Figure 1A:
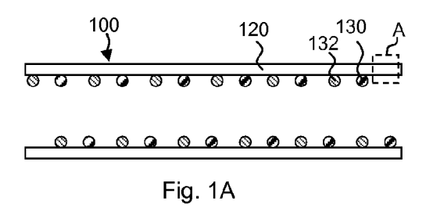
FIG. 1A is a schematic longitudinal cross sectional view of a portion of a medical lead, in accordance with an embodiment of the invention.

Various specific embodiments of the invention will now be described with further reference to the drawings. FIG. 1A is a schematic longitudinal cross sectional view of an insulated (non-electrode) portion of a medical lead 100 in accordance with the invention (which may correspond, for example, to an insulated portion of one of the leads shown in FIG. 6, among many other possibilities). The portion of the lead shown includes a first coiled conductor 130 and a second coiled conductor 132 disposed in a co-radial arrangement with one another. An advantage of a coiled configuration for the conductors 130, 132 is that the various types of movements experienced by the lead in vivo are converted into torsion, which the metals that are typically used to form the coils can readily tolerate. The coiled conductors 130, 132 may be made, for example, of stainless steel, Eigiloy, or MP35N, among other suitable conductive materials. The coiled conductors 130, 132 may each be provided with a layer of insulating material, for example, a low-friction polymeric material such as polytetrafluoroethylene (PTFE) or ethylene-tetrafluoroethylene fluoropolymer (ETFE), among other low-friction fluoropolymers and non-fluoropolymers.

The coiled conductors 130,132 are disposed within a tubular insulation layer 120, which acts to chemically, mechanically and electrically insulate the coiled conductors from the external environment and can also provide the lead with desirable mechanical characteristics such as torqueability.

The tubular insulation layer 120 may comprise a single material, for example a SIBC containing material. As discussed in more detail below, SIBC containing material for use in the invention may comprise, in addition to one or more SIBC's (e.g., SIBS, etc.), one or more optional supplemental agents, for example, selected from processing aids, blending polymers, particulate agents and therapeutic agents, among others. Such a tubular insulation layer 120 may be, for example, solvent coated over the coiled conductors 130,132, extruded over the coiled conductors 130, 132, or first extruded and then inserted over the coiled conductors 130,132, among other possibilities. In the latter case, the pre-formed tubular insulation layer 120 may be bonded to the insulating material on the coiled conductors 130, 132, for example, by a suitable elevated temperature process such as laser bonding (where the insulating material is a thermoplastic material).

The tubular insulation layer 120 may also comprise two or more material regions, for example, two or more layers of material, which may form two or more coaxial tubular material regions.

Figure 1B:
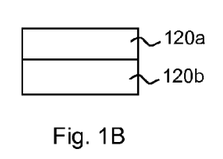
FIGS. 1B and 1C are alternative expanded views of area A from FIG. 1A, in accordance with two embodiments of the invention.

For example, FIG. 1B is an expanded view of area "A" of FIG. 1A in accordance with an embodiment of the invention and includes two coaxial tubular material regions 120a and 120b of differing composition. The outer material region 120a may be, for example, an SIBC containing material such as that previously described. The inner material region 120b may be, for example, a non-SIBC TPE containing material. As discussed in more detail below, non-SIBC TPE containing materials for use in the invention may comprise, in addition to one or more non-SIBC TPE's (e.g., one or more TPU's, for instance, a polyether polyurethane such as Pellethane®, etc.), one or more optional supplemental agents.

The outer material region 120a may be, for example, solvent coated over the inner material region 120b, extruded over the inner material region 120b, co-extruded with the inner material region 120b, or first extruded and then inserted over the inner material region 120b, among other possibilities. Because the inner and outer material regions 120a,120b are thermoplastic materials, the outer material region 120a may be fused to the inner material region 120b by a suitable elevated temperature process, for instance, a laser bonding process. The use of laser bonding creates, for instance, the potential for high speed manufacturing of leads, reduced assembly time and/or improved production yield.

Figure 1C:
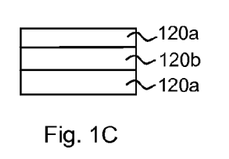

As another example, FIG. 1C is an expanded view of area "A" of FIG. 1A in accordance with an alternative embodiment of the invention and includes three coaxial tubular material regions of differing composition. The inner and outer material regions 120a may be, for example, an SIBC containing material in accordance with the invention. The intervening region 120b may be, for example, a non-SIBC TPE containing material in accordance with the invention.

Figure 5:
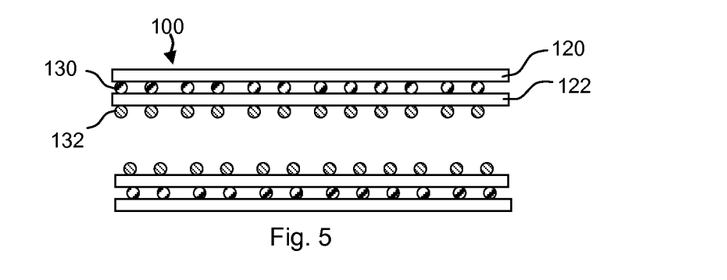
FIG. 5 is a schematic longitudinal cross sectional view of a portion of a medical lead, in accordance with yet another embodiment of the invention.

Like FIG. 1A, FIG. 5 is a schematic longitudinal cross sectional view of an insulated portion of a medical lead 100 in accordance with the invention that includes first and second coiled conductors 130, 132, each of which may be provided with layer of a suitable insulating material, for example, a fluoropolymer such as those described above, among others.

Unlike FIG. 1A, the first and second coiled conductors 130,132 in FIG. 5 are disposed in a co-axial (rather than co-radial) arrangement with one another. The inner coiled conductor 132 is provided with a tubular insulation layer 122, which acts to insulate the coiled conductor 132 from the external environment (and from the outer coiled conductor 130 as well). The inner tubular insulation layer 122 may also provide the lead with desirable mechanical characteristics such as torqueability. Examples of materials for the inner tubular insulation layer 122 include, for example, silicone rubber, PTFE, ETFE or a TPE containing material, for instance, a TPU or a SIBC containing material in accordance with the invention, among others.

The outer coiled conductor 130 is disposed over the inner tubular insulation layer 122, and an outer tubular insulation layer 120 is disposed over the outer coiled conductor 130. Like the tubular insulation layer of FIG. 1A, the outer tubular insulation layer 120 of FIG. 5 may be formed of a single material, for example, a SIBC containing material. The outer tubular insulation layer 120 of FIG. 5 may also comprise two or more material regions, for example, two or more layers of material, which may form two or more coaxial tubular material regions. Specific examples of two-material and three-material regions suitable for use in the outer tubular insulation layer 120 of FIG. 5 are described in conjunction with FIGS. 1B and 1C above.

Figure 2A:
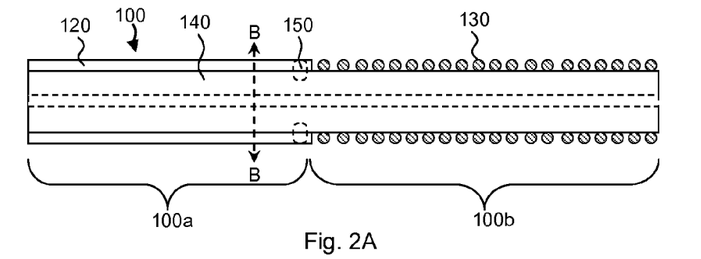
FIG. 2A is a schematic longitudinal cross sectional view of a portion of a medical lead, in accordance with another embodiment of the invention.

FIG. 2A is a schematic longitudinal cross sectional view of an insulated (non-electrode) portion 100a and a non-insulated (electrode) portion 100b of a medical lead 100 in accordance with the invention. The portion of the lead 100 shown includes a polymer containing inner elongated member 140 (which includes one or more lumens along its length). Disposed over the right-hand portion 100b of the inner elongated member 140 is a coiled conductor 130 which may act, for example, as a shocking/defibrillation electrode for the medical lead 100. Because it acts as an electrode, the coiled conductor 130 is either uncoated or coated with a conductive layer (e.g., a layer of iridium oxide, etc.). Disposed over the left-hand portion 100a of the inner elongated member 140 is a tubular covering 120, which acts to smooth the transition between the non-electrode portion 100a and the electrode portion 100b (i.e., the tubular covering 120 is provided to create a continuous diameter for the device). For example, the thickness of the tubular covering 120 can be the same as the diameter of the conductor forming the coil 130, such that the maximum diameter of portion 100a matches that of portion 100b. (In addition to ensuring a smooth the transition between the electrode and non-electrode bearing portions 100b,100a, the tubular covering 120 can also assist in insulating any conductor(s) lying within the inner elongated member 140, and may improve the mechanical characteristics of the lead, including such as torqueability.) The material for the tubular covering 120 may be, for example, a TPE containing material (e.g., a TPU or a SIBC containing material, etc.) in accordance with the invention. Such a tubular covering 120 material may be, for example, solvent coated over the inner elongated member 140, extruded over the inner elongated member 140, co-extruded with the inner elongated member 140, or first extruded and then inserted over the inner elongated member 140, among other possibilities.

Figure 2B:
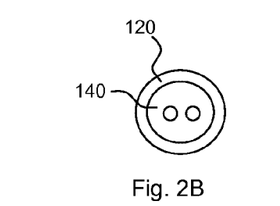
FIG. 2B is a cross section of the device of FIG. 2A, taken along line B-B.

FIG. 2B is a cross section of the device of FIG. 2A, taken along line B-B, and shows a two-lumen inner elongated member 140 with tubular covering 120. The lumens of the inner elongated member 140 may accommodate, for example, a guidewire and a conductor, two conductors, etc. Other configurations, including inner elongated members with one, four, five, six, seven, eight, etc. lumens are also possible. The material for the inner elongated member 140 may be, for example, a silicone containing material or a material containing a TPE such as a TPU or a SIBC such as SIBS, among other possibilities. An advantage associated with the use of a TPE for the inner elongated member 140 is that the member 140 can be extruded (a thermoplastic process). Another advantage associated with the use of a TPE for the inner elongated member 140 is that the inner elongated member 140 can be inserted into the tubular covering 120, and the tubular covering 120 can be fused to the inner elongated member 140 by a suitable elevated temperature process, for instance, a laser bonding process.

Such a process may be used, for example, to create a ring shaped thermally fused region 150 as shown in FIG. 2A (e.g., by rotating the device under laser irradiation). By extending the fused region entirely around the circumference of device, an effective seal is formed between the tubular covering 120 and inner elongated member 140. Of course a laser bonding process can produce thermally fused regions of various shapes in addition to ring shaped regions. For example, the tubular covering 120 can be "spot-fused" to the inner elongated member 140 at various locations (in a process analogous to spot-welding) to prevent unacceptable levels of movement between the tubular covering 120 and inner elongated member 140 during implantation.

Figure 3A:
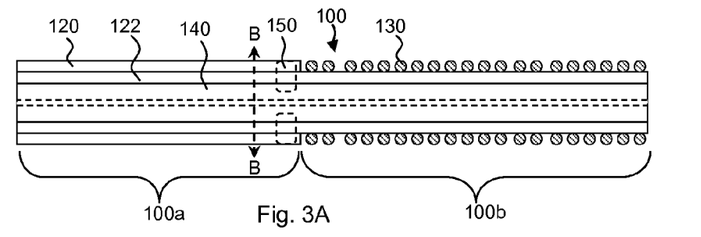
FIG. 3A is a schematic longitudinal cross sectional view of a portion of a medical lead, in accordance with another embodiment of the invention.
Figure 3B:
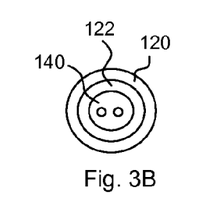
FIG. 3B is a cross section of the device of FIG. 3A, taken along line B-B.

FIG. 3A is a schematic longitudinal cross sectional view of an insulated (non-electrode) portion 100a and a non-insulated (electrode) portion 100b of a medical lead 100 in accordance with the invention. FIG. 3B is a cross section of the device of FIG. 3A, taken along line B-B. Like the device of FIGS. 2A-2B, the device of FIGS. 3A-3B includes a polymer-containing two-lumen inner elongated member 140, a coiled conductor 130, and a tubular covering 120. The device of FIGS. 3A-3B, however, is further provided with an additional tubular covering 122 that surrounds the inner elongated member 140. The inner elongated member 140 may be formed, for example, from a silicone containing material or a material containing a TPE such as a TPU or a SIBC such as SIBS, among other possibilities. The tubular covering 120 and the additional tubular covering 122 may be formed, for example, from a material containing a TPE such as a TPU or a SIBC such as SIBS, among other possibilities. In a specific example, both the tubular covering 120 and the additional tubular covering 122 are formed from SIBC containing materials such as SIBS, such that the inner elongated member 140 is covered over its entire length by an SIBC containing material (e.g., to provide environmental protection, etc.).

As above, advantages associated with the use of a TPE for the inner elongated member 140 include the ability to extrude the member 140 and the ability to fuse an assembly consisting of a previously formed inner elongated member 140, tubular covering 120 and additional tubular covering 122 using a suitable elevated temperature process, for instance, a laser bonding process. Such a process may result, for example, in a ring shaped thermally fused region 150 as shown in FIG. 3A.

Figure 4:
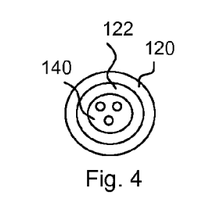
FIG. 4 is an alternative cross section to that of FIG. 3B.

FIG. 4 is an alternative embodiment of the cross section of FIG. 3B which shows an inner elongated member 140 having three lumens. Other configurations, including inner elongated members with one, four, five, six, seven, eight, etc. lumens are also possible.

In certain embodiments of the invention, the outer insulation layers of the devices, including insulation layers formed from SIBC containing materials, may be treated to increase their lubricity. For example, the outer insulation layers may be coated with a parylene layer or plasma grafted with a biocompatible monomer for this purpose, examples of which include hexamethylene disilazane, $C_3F_8$ (octafluoropropane), trifluoromethane and octafluorocyclobutane, among others.

As noted above, in various embodiments, the polymer containing materials that are employed in the present invention, including SIBC containing materials and non-SIBC TPE containing materials, may be blended or otherwise combined with one or more optional supplemental agents. For example, polymers such as SIBC's and non-SIBC TPE's may be blended with one or more of the following agents, among others: processing aids, blending polymers, particulate agents and therapeutic agents.

Examples of processing aids include, for example, biocompatible plasticizers, which may be provided in order to enhance the extrudability of the material and may be selected from one or more of the following organic plasticizers, among others: dioxane, phthalate derivatives such as dimethyl, diethyl and dibutyl phthalate, glycerol, glycols such as polypropylene, propylene, polyethylene and ethylene glycol, citrate esters such as tributyl, triethyl, triacetyl, acetyl triethyl, and acetyl tributyl citrates, surfactants such as sodium dodecyl sulfate and polyoxymethylene (20) sorbitan and polyoxyethylene (20) sorbitan monooleate. Preferred organic plasticizers include polyethylene glycols (including polyethylene glycols with molecular weights preferably from about 200 to 6,000), dioxane and citrate esters. Citrate esters are renewable resource derivatives derived from citric acid, a tribasic monohydroxy acid (2-hydroxy-1,2,3-propanetricarboxylic acid), $C_6H_8O_7$, and a natural constituent and common metabolite of plants and animals. They are non-toxic and have been used as plasticizers with a variety of different polymers.

Examples of blending polymers may be selected from one or more of the following, among others: SIBS with varying styrene and isobutylene content, thermoplastic polyurethanes with various hard and soft segments including those comprising soft segments selected from polydimethylsiloxane, polyisobutylene, polyether and polycarbonate segments.

Examples of particulate materials include, for example, organically modified silicates. Such agents may act to create a tortuous pathway for moisture thereby decreasing the moisture permeability of the region. Moreover, such agents may maintain the strength and increase the modulus of the material. Supplemental particulate agents further include agents such as alumina, silver nanoparticles, silicate/alumina/silver nanoparticle composites, and carbon nanofibers, among others.

In some embodiments, one or more therapeutic agents are included within (e.g., blended with) or attached to (e.g., covalently or non-covalently bound to) to the polymer containing materials of the invention. Therapeutic agents may be selected, for example, from one or more of the following, among others: blood compatibilizing agents such as heparin, tetraglyme, diamond like carbon, polyethylene glycol, hyaluronic acid, chitosan, methyl cellulose, poly(ethylene oxide), poly(vinyl pyrrolidone), phosphorylcholine and Taurine containing monomers, among others, pro-healing agent such as such as GRGD, YGSIR and GFOGER peptides and collagen, antithrombotic agents such as sulfated collagen, heparin, albumin and hirudin, steroids such as dexamethasone, as well as phospholipids.

Where a therapeutic agent is present, a wide range of loadings may be used in conjunction with the medical devices of the present invention. Typical therapeutic agent loadings range, for example, from than 1 wt % or less to 2 wt % to 5 wt % to 10 wt % to 25 wt % or more of the polymer containing materials.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable and insertable medical device for electrical stimulation comprising:
    an internal member selected from an elongated conductor and an electronic signal generating component; and
    a first insulating region disposed over said internal member, wherein said first insulating region comprises a blend of a first copolymer having a styrene content that ranges from 15 to 21 mol %, and a second copolymer having a styrene content that ranges from 22 to 50 mol %, wherein the blend is a mixture of the first copolymer and the second copolymer, the first copolymer and the second copolymer retaining their chemical compositions.

2. The medical device of claim 1, wherein the internal member is an elongated conductor.

3. The medical device of claim 1, wherein the internal member is an electronic signal generating component.

4. The medical device of claim 1, further comprising a therapeutic agent disposed in the first insulating region.

5. The medical device of claim 1, further comprising a second insulating region disposed over the first insulating region, wherein the second insulating region comprises a thermoplastic polymer other than a copolymer that comprises styrene and isobutylene.

6. The medical device of claim 1, further comprising a second insulating region disposed between the first insulating region and the internal member, wherein the second insulating region comprises a thermoplastic polymer other than a copolymer that comprises styrene and isobutylene.

7. The medical device of claim 6, wherein the internal member is an elongated conductor and wherein the second region corresponds to a multi-lumen extrusion within which the elongated conductor is disposed and the first insulating region corresponds to a tubular insulation layer disposed around the multi-lumen extrusion.

8. The medical device of claim 7, wherein a coiled electrode is disposed around a first portion of the multi-lumen extrusion and wherein the tubular insulation layer is disposed around a second portion of the multi-lumen extrusion that is adjacent to the first portion.

9. The medical device of claim 6, wherein the first insulating region is directly fused to the second insulating region.

10. The medical device of claim 6, further comprising a third insulating region disposed between the second insulating region and the internal member, wherein the third insulating region comprises a copolymer that comprises styrene and isobutylene.

11. The medical device of claim 10, wherein the third insulating region comprises a blend of the first and second copolymers, wherein the blend is a mixture of the first copolymer and the second copolymer, the first copolymer and the second copolymer retaining their chemical compositions.

12. The medical device of claim 1, wherein at least one of the first copolymer and the second copolymer comprises one or more polystyrene blocks and one or more polyisobutylene blocks.

13. The medical device of claim 1, wherein the first insulating region further includes a polymer that does not include styrene.

14. The medical device of claim 13, wherein the polymer that does not include styrene is selected from the group consisting of a polyurethane that includes a polyisobutylene soft segment and a polyurethane that includes a polydimethylsiloxane segment.

15. An implantable and insertable medical device for electrical stimulation comprising:
an internal member selected from an elongated conductor and an electronic signal generating component; and
a first insulating region disposed over said internal member, wherein said first insulating region consists of a blend of a first copolymer having a styrene content that ranges from 15 to 21 mol %, and a second copolymer having a styrene content that ranges from 22 to 50 mol %, wherein the blend is a mixture of the first copolymer and the second copolymer, the first copolymer and the second copolymer retaining their chemical compositions.

16. The medical device of claim 15, wherein the internal member is an electronic signal generating component.

17. The medical device of claim 15, wherein the internal member is an elongated conductor.

18. The medical device of claim 17, wherein the first and second copolymers are thermally extruded in a pre-blending step prior to thermal extrusion into a single-lumen or multi-lumen device component that provides the first insulating region.

19. A method for making an implantable and insertable medical device for electrical stimulation, the medical device including an internal member selected from an elongated conductor and an electronic signal generating component, the method comprising:
thermally extruding a blend of a first copolymer and a second copolymer to form an insulating region disposed over the internal member, wherein the first and second copolymers each include styrene and isobutylene, the styrene content in the first copolymer ranging from 15 to 21 mol %, and the styrene content in the second copolymer ranging from 22 to 50 mol %, wherein the insulating region is a mixture of the first copolymer and the second copolymer, the first copolymer and the second copolymer retaining their chemical compositions.

20. The method of claim 19, further including thermally extruding the first and second copolymers in a pre-blending step prior to thermal extruding the first and second copolymers to form the insulating region.

* * * * *